(12) United States Patent
Singh et al.

(10) Patent No.: US 7,270,973 B2
(45) Date of Patent: Sep. 18, 2007

(54) CATALYTIC ENZYME-MODIFIED TEXTILES FOR ACTIVE PROTECTION FROM TOXINS

(75) Inventors: Alok Singh, Springfield, VA (US); Walter J. Dressick, Fort Washington, MD (US); Yongwoo Lee, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 275 days.

(21) Appl. No.: 10/849,621

(22) Filed: May 20, 2004

(65) Prior Publication Data

US 2005/0136523 A1 Jun. 23, 2005

Related U.S. Application Data

(63) Continuation-in-part of application No. 10/750,637, filed on Dec. 23, 2003, now Pat. No. 7,067,294.

(51) Int. Cl.
*C12Q 1/34* (2006.01)

(52) U.S. Cl. .................. 435/18; 8/51; 8/115; 8/401
(58) Field of Classification Search .................. 435/18; 8/115.51, 401
See application file for complete search history.

(56) References Cited

U.S. PATENT DOCUMENTS

| | | | |
|---|---|---|---|
| 5,663,387 A | 9/1997 | Singh | |
| 6,080,566 A | 6/2000 | Cheng et al. | |
| 6,469,145 B1 | 10/2002 | Rastogi et al. | |
| 7,067,294 B2 * | 6/2006 | Singh et al. | 435/174 |

OTHER PUBLICATIONS

Lee, Y. et al. Sustained Enzyme Activity of Organophosphorus Hydrolase in Polymer Encased Multilayer Assemblies. Langmuir 2003, 19, 1330-1336.*
Santos J. et al. Polyelectrolyte Assisted Immobilization of Active Enzymes on Glass Beads. Langmuir 2001 17, 5361-5367.*
Geraldine F. Drevon, Karsten Danielmeier, William Federspiel, Donna. Stolz, Douglas A. Wicks, Poli C. Yu, Alan J. Russell, "High-Activity Enzyme-Polyurethane Coatings," Biotech. Bioeng., 2002, 79 (7) 785-794.
Geraldine F. Drevon & Alan J. Russell, "Irreversible Immobilization of Disopropylfluorophosphatase in Polyurethane Polymers," Biomacromolecules, 2000, vol. 1, No. 4, 571-576.
Gero Decher, "Fuzzy Nanoassemblies: Toward Layered Polymeric Multicomposites," Science, 1997, vol. 277, 1232-1237.
Stephan T. Dubas & Joseph B. Schlenoff, "Swelling and Smoothing of Polyelectrolyte Multilayers by Salt," Langmuir, 2001, 17, 7725-7727.
Yuri Lvov, Alexei A. Antipov, Arif Mamedov, Helmuth Mohwald & Gleb B. Sukhorukov, "Urease Encapsulation in Nanoorganized Microshells," Nano Lett., 2001, vol. 1, No. 3, 125-128.
Steven L. Regen, Jae-Sup Shin, James F. Hainfeld & Joseph S. Wall, "Ghost Vesicles," J. Am. Chem. Soc., 1984, 106, 5756-5757.
John P. Santos, Eric R. Welsh, Bruce P. Gaber & Alok Singh, "Polyelectrolyte-Assisted Immobilization of Active Enzymes on Glass Beads," Langmuir, 2001, 17, 5361-5367.
Yongwoo Lee, Ivan Stanish, Vipin Rastogi, Tu-Chen Cheng & Alok Singh, "Sustained Enzyme Activity of Organophosphorus Hydrolase in Polymer Encased Multilayer Assemblies," Langmuir, 2003, 19, 1330-1336.
Wei Zhao, Wanhoon Ma, Chencheng Chen, Jincai Zhao & Zhigang Shuai, "Efficient Degradation of Toxic Organic Pollutants with $Ni_2O_3/TiO(2-x)B_x$ under Visible Irradiation," J. Am. Chem. Soc., 2004, 126, 4782-4783.
Terrence G. Vargo, Joseph A. Gardella Jr., Jeffrey M. Calvert, Mu-San Chen, "Adhesive Electroless Metallization of Fluoropolymeric Substrates," Science, 1993, 262, 1711-1712.
Mu-San Chen, Charles S. Dulcey, Susan L. Brandow, Donovan N. Leonard, Walter J. Dressick, Jeffrey M. Calvert & Christopher W. Sims, "Patterned Metallization of Diamond and Alumina Substrates," J. Electrochem. Soc., 2000, 147 (7) 2607-2610.
Jian Lin, Shuyi Qiu, Kim Lewis & Alexander M. Klibanov, "Bactericidal Properties of Flat Surfaces and Nanoparticles Derivatized with Alkylated Polyethylenimines," Biotechnol. Prog., 2002, 18, 1082-1086.
G. Crini, G. Torri, M. Guerrini, B. Martel, Y. Lekchiri & M. Morcellet, "Linear Cyclodextrin-Poly(vinylamine): Synthesis and NMR Characterization," Eur. Polym. J., 1997, 33 (7) 1143-1151.
Anja Ruebner, Gary L. Statton, Mike R. James, "Synthesis of a linear polymer with pendent y-cyclodextrins," Macromol. Chem. Phys., 2000, 201, 1185-1188.

* cited by examiner

*Primary Examiner*—Ralph Gitomer
(74) *Attorney, Agent, or Firm*—Stephen T. Hunnius; John J. Karasek

(57) ABSTRACT

Catalytic enzyme-modified textiles are disclosed for providing protection from chemical exposure. The textiles are composed of a cloth substrate, at least one polyelectrolyte layer, at least one enzyme layer to degrade the chemical agent, and at least one capping layer. Also disclosed is the related method for making catalytic enzyme-modified textiles.

15 Claims, 1 Drawing Sheet

CATALYTIC ENZYME-MODIFIED TEXTILES FOR ACTIVE PROTECTION FROM TOXINS

This is a continuation-in-part application of application Ser. No. 10/750,637 filed on Dec. 23, 2003, issued on Jun. 27, 2006 as U.S. Pat. No. 7,067,294, the entire contents of which are incorporated herein by reference.

BACKGROUND

1. Field of the Invention

The present invention relates to catalytic enzyme-modified textiles, and, more specifically, to catalytic enzyme-modified textiles for active protection from air or water borne toxins by active passivation and adsorption of toxic materials. Toxins include chemical and biological agents and toxic industrial chemicals.

2. Description of the Prior Art

There is an urgent need for the development of effective means to protect people and the environment from the exposures of toxic chemicals and other threat agents irrespective of the cause of exposure, accidental or due to terrorist act. Moreover, there is a need to protect people from exposure to chemicals during their work and from prolonged exposure to small amounts of toxic chemicals (especially in a closed environment). Long-term exposure to chemicals at low levels or persistent encounters with small quantities of toxic chemicals may be more harmful than one time exposure at higher levels. Examples of such chemicals are pesticide and chemical warfare agents, and toxic vapors from hydrolyzed chemical agents (e.g., HF and HCN).

The existing technologies use barrier protection involving materials of high absorbing capacity to protect people and the environment. The most widely used adsorbent is active charcoal, which leads to the development of bulky materials. Materials used in barrier protection are bulky and have only one useful life cycle. While the barrier technologies provide adequate protection, they have the serious technical problem of off gassing and disposal of the materials at the end of their active life cycle because of the presence of toxic materials in concentrated form. Other concerns include weight, capacity, and inconvenience during practical use.

Many existing protective garments are heavy, bulky, and uncomfortable. They are usually made from rubber and other polymers. These garments generally provide passive, rather than active protection. That is, they act simply as barrier layers to prevent contact of the chemical with the person's body. Because they do not self-decontaminate after exposure to a chemical toxin, current protective garments require cleaning after use before they can be used again or before disposal in the case of single use garments.

Another existing technology regarding toxic chemicals is the use of enzymes. Enzymes are the most effective catalyst against chemical agents but have limited long-term stability. Also, they often lose their catalytic activity during immobilization steps. See G. F. Drevon, K. Danielmeier, W. Federspiel, D. B. Stolz, D. A. Wicks, P. C. Yu, A. J. Russell, "High-Activity Enzyme-Polyurethane Coatings," *Biotechnology and Bioengineering*, 79 (7) 785-794 (2002); and G. F. Drevon & A. J. Russell, "Irreversible Immobilization of Diisopropylfluorophosphatase in Polyurethane Polymers," *Biomacromolecules*, 1 (4) 571-576 (2000), the entire contents of both are incorporated herein by reference. Lack of stability and loss of catalytic activity render enzymes unsuitable for protection applications. Several techniques have been reported for stabilizing the enzymes—most of them focusing on their immobilization to a suitable substrate. However, chemical linking to the surface causes the enzymes to lose their activity substantially. Non-covalent immobilization of enzymes on vesicles provides an effective means to retain enzyme activity. See U.S. Pat. No. 5,663,387 to Singh, the entire contents of which is incorporated herein by reference. Deposition of a single layer of enzymes on a surface is good for a sensor application, but not adequate for chemical agent passivation applications, which require a larger amount of enzymes to effectively hydrolyze the toxic chemicals.

SUMMARY

The aforementioned problems are overcome by the present invention wherein bioactive catalytic enzyme-modified textiles for providing protection from chemical exposure that are stable and retain their catalytic activity comprise a cloth substrate, at least one polyelectrolyte layer, at least one enzyme layer to degrade the chemical agent, and an end-capping layer. The present invention provides novel, bioactive, textiles for providing protection against chemical agents, which are more effective than barrier protection. These textiles can be used to develop lighter weight clothing to adsorb and passivate toxins before they reach the human body. The textiles of the present invention can be used for reusable clothing that decontaminates itself after exposure to toxins and can be worn multiple times or for disposable clothing and wipes intended for a single use that decontaminate themselves without harming the environment.

In a preferred embodiment, the present invention takes advantage of superior catalytic activity of enzymes by immobilizing them within polyelectrolyte multilayers (PEMs). The technique for forming multilayers is simple and effective as polyelectrolytes of opposing polarity are alternatively deposited through neutralization and overcompensation of their charges. See G. Decher, "Fuzzy Nanoassemblies: Toward Layered Polymeric Multicomposites," *Science*, 277, 1232-1237 (1997), the entire contents of which is incorporated herein by reference. Enzymes immobilized in the multilayers are easily accessible to the incoming toxic materials and, thus, passivate them efficiently. A capping agent provides stability to the multilayers, keeps enzymes protected in adverse working environments, and attracts the toxic agents to facilitate contact with the catalytic sites.

The present invention provides several advantages over the prior art. It leads to enhanced enzyme shelf life under normal storage conditions. It allows incorporation of multiple components into multilayers to provide add-on capabilities to the packaged system. It is lightweight, robust, sturdy, disposable, self-decontaminating, and cost-effective. It offers versatility as it can be designed for use on various materials.

BRIEF DESCRIPTION OF THE DRAWINGS

These and other objects, features, and advantages of the invention, as well as the invention itself, will become better understood by reference to the following detailed description, appended claims, and accompanying drawing where:

DETAILED DESCRIPTION

Figure 1:
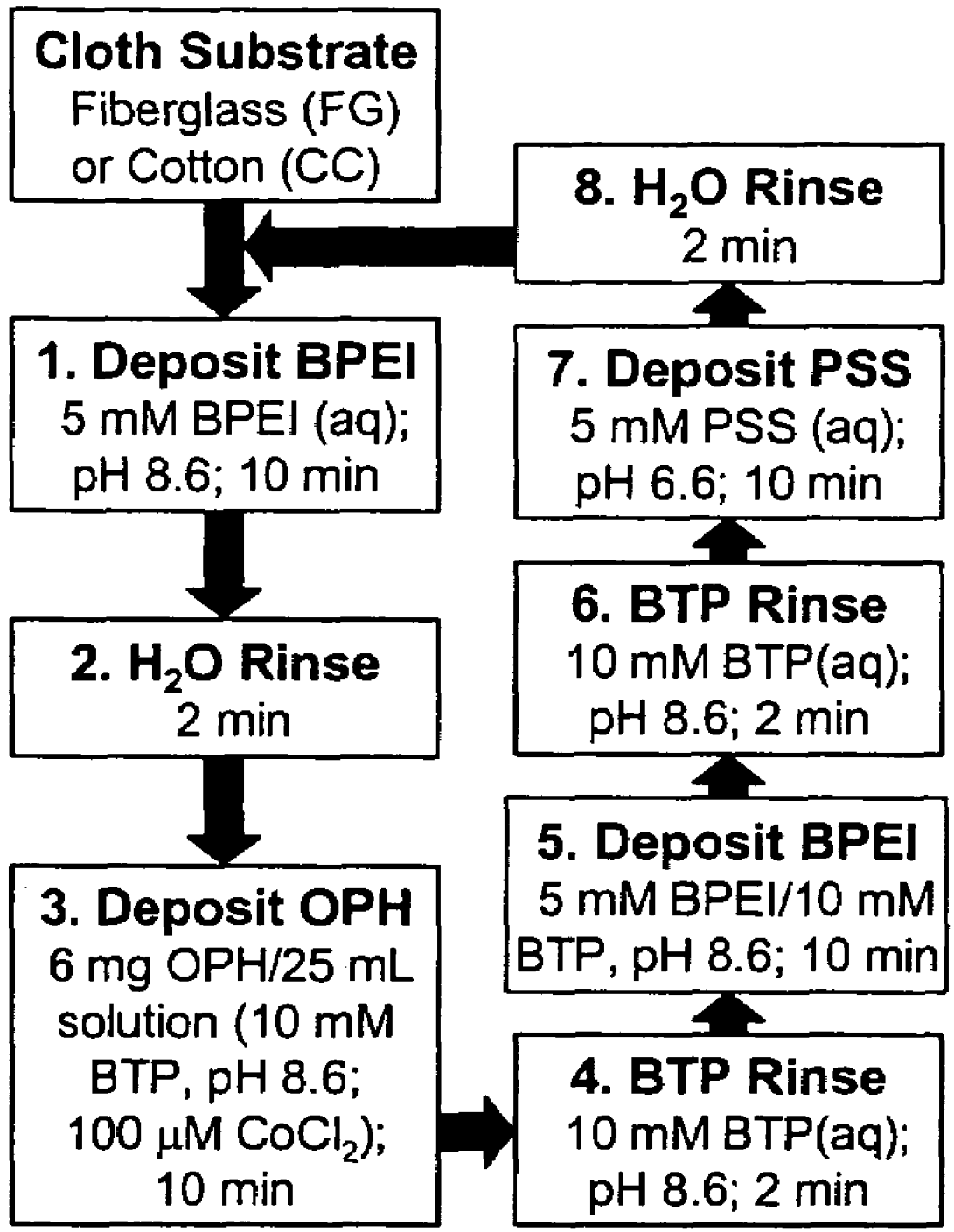
FIG. 1 shows an OPH–PEM preparation scheme. The completion of step 6 marks the end of each OPH deposition cycle. [BPEI] and [PSS] quoted are calculated based on monomer units of each polymer.

The core of the present invention is the packaging of essential components within alternate layers, or within a single layer, to produce bioactive textiles and the stabilization of catalytic components and multilayer assemblies to make them durable without losing their performance. Catalysts are immobilized within polyelectrolytes to degrade chemical agents and selectively capture degradation products. A capping layer provides structural robustness and resists aggressive physical and chemical perturbations.

In a preferred embodiment, the catalysts include enzymes, classless non-specific catalysts, and adsorbent particles. Preferred enzymes are those that are superior catalysts for degrading chemical agents with high turnover numbers. Based on the need and application, any commercially available enzyme can be used. Examples of preferred enzymes include organophosphorous hydrolase (OPH) (EC 3.1.8.1), organophosphorous acid anhydrolase (OPAA) (EC 3.1.8.2), diisopropylfluorophosphatase (DFPase) (EC 3.1.8.2), phosphotriesterases (PTE) (EC 3.1.8), and combinations of enzymes capable of passivating a large number of toxic agents. A combination of OPH or PTE with OPAA will destroy most of the chemical agents used in warfare. OPH is preferred due to its good activity, stability, and ease of use. Several other enzymes can be used, including paraoxonase, aryldialkylphosphatase, and bacterial HD hydrolase.

Classless non-specific catalysts catalyze hydrolysis of chemical agents at a slower rate than enzymes. Examples of preferred classless non-specific catalysts include metal chelated catalytic particles (MCCP) such as metal chelated polymers (e.g., N-substituted ethylenediamine-copper (EDA-$Cu^{2+}$) complexes), silica particles, and titania ($TiO_2$) particles. $TiO_2$ particles are useful for light induced degradation of chemical and biological agents because they have appropriate oxidizing or reducing power during UV illumination due to their band gap so as to decompose target particles. $TiO_2$ bandgap can be tuned to allow visible light excitation through particle doping (W. Zhao, W. Ma, C. Chen, J. Zhao, Z. Shuai, "Efficient Degradation of Toxic Organic Pollutants with $Ni_2O_3/TiO_{2-x}B_x$ under Visible Irradiation," *J. Am. Chem. Soc.*, 126, 4782-4783 (2004), the entire contents of which is incorporated herein by reference). MCCPs are useful in degrading those chemical agents that are not degraded by enzymes. Multilayers will provide enough chemical protection and separation to $TiO_2$ and enzymes that they can function independently.

Adsorbent particles are functional catalytic particles (FCP) made by incorporating quaternary ammonium surfactant to silica microparticles. Also, acidic or basic alumina may be used to capture degradation products and biological particles. FCPs partially hydrolyze chemical agents and selectively capture degradation products.

Multilayers can be fabricated on any sort of material, comprised of either natural or man-made polymer or glass, which can adsorb the charged polymer components of the multilayers. Preferred examples of materials include fiberglass and cotton. Man-made substances, such as rayon, nylon, etc., can also be used. Cotton may be used unmodified or modified with cyclodextrin or an amine. The material can be used in many forms, including cloth, thread, string, string knitted to cloth, etc.

Multilayers can also be fabricated on materials that are normally thought of as inert, provided that their surface is first chemically modified to generate functional groups that can support subsequent adsorption of the charged polymers or enzymes. For example, films of polytetrafluoroethylene (PTFE) or Teflon® are normally non-adhesive materials; i.e, it is difficult to adsorb other materials to these films. However, brief oxidation of the surface using a plasma creates highly acidic surface hydroxyl groups, which readily deprotonate to form anionic functional groups on the surface. Aminosiloxane self-assembled monolayers can be chemisorbed to these species, providing a reactive amine terminated monolayer coating on the PTFE or Teflon® film. These reactive amines can be used to bind other materials, such as metals, with good adhesion to the underlying PTFE or Teflon® (T. G. Vargo, J. A. Gardella Jr., J. M. Calvert, M-S. Chen, "Adhesive Electroless Metallization of Fluoropolymeric Substrates," *Science*, 262, 1711-1712 (1993), the entire contents of which are incorporated herein by reference). Because the surface hydroxyl groups present on plasma oxidized films of PTFE or Teflon® deprotonate in water to form surface anions, adsorption of a cationic polyelectrolyte such as the branched polyethylenimine (BPEI), which is used as the first layer of the multilayer films described below, on these surfaces is possible. In addition, the possibility also exists to use a PTFE or Teflon® film bearing a chemisorbed aminosiloxane film as a base positively charged film in the multilayer assemblies described below. Such an aminosiloxane film might be used to directly bind an enzyme layer during the fabrication of a multilayer film. Alternatively, an aminosiloxane film might be used to bind a layer of anionic polyelectrolytes, such as polystyrenesulfonate (PSS), which could then serve as a base layer for binding the first layer of BPEI.

A second example of a material that is generally inert towards chemical reactivity is diamond. However, through gentle plasma oxidation, surface OH groups can also be created on the diamond surface. Once again, such groups can serve to anchor other materials, such as aminosiloxane films (M-S. Chen, C. S. Dulcey, S. L. Brandow, D. N. Leonard, W. J. Dressick, J. M. Calvert, C. W. Sims, "Patterned Metallization of Diamond and Alumina Substrates," *J. Electrochem. Soc.*, 147 (7) 2607-2610 (2000), the entire contents of which is incorporated herein by reference), that serve to impart chemical reactivity or binding abilities to the diamond substrate.

A molecular "glue" is used to hold all the active catalytic components together, to stabilize enzymes, and to provide adequate adhesion of the assemblies to the support materials without involving any chemical reaction. Polyelectrolytes, by virtue of available cationic or anionic functionalities in abundance, provide an excellent means to glue the molecular components. Cooperativity and electrostatic interactions, hydrogen bonding, and/or Van der Waals interaction between anionic and cationic sites leads to the formation of strong association of multilayers. Examples of polyelectrolytes that can be used include commercially available polyelectrolytes, branched or linear polyethyleneimine (PEI), polyacrylic acid (PAA), polymethacrylic acid (PMA), polystyrene sulfonate (PSS), polydiallyl dimethyl ammonium chloride (PDDA), polyvinylpyridine (PVP), polyvinyl sulfate (PVS), polyallylamine hydrochloride (PAH), their chemically altered derivatives, and any combination thereof.

The surface is chemically tuned through composition of the polyelectrolyte deposition solution. For example, in neutral or basic solution where the pH is greater than the isoelectric point of silica or glass, the silica or glass surface is negatively charged and readily adsorbs cationic polyelectrolytes like BPEI. However, if one needed to work in highly acidic media due to stability or solubility considerations for the polyelectrolyte to be deposited, one could modify the surface with an aminosiloxane film to create a positively charged surface. One could then bind a polyelectrolyte such as polystyrene sulfonate (PSS), which remains an anionic species even in highly acidic solution (e.g., pH ~1), to recreate a negatively charged surface suitable for deposition of further polyelectrolyte layers at low pH.

The deposition method may be variable. For example, a simple dip coating procedure involving immersion of the substrate to be treated in the appropriate polyelectrolyte of enzyme solutions provided the best performing cloths with respect to catalytic methyl parathion (MPT) hydrolysis to paranitrophenol (PNP) in solution. However, spray coating or spin coating methods, which are readily amenable for commercial applications, can also be used to fabricate the catalytic multilayers on the substrates. These latter methods produced multilayer films exhibiting less catalytic activity than samples prepared by dip coating. However, since no attempt was made to optimize multilayer deposition according to spin coating or spray coating methods, further improvement in catalytic ability should be possible for such films.

A capping agent is used to encase the catalytic components. The capping agent provides stability to the catalytic components, keeps the enzyme architecture dimensionally protected in adverse working environments, and ideally attracts the toxic agents to facilitate contact with the catalytic sites. In a preferred embodiment, pH- and photo-polymerizable monomers and/or metal-ion crosslinked systems are used as capping agents. In an even more preferred embodiment, the capping agent is selected from the group consisting of 1,2-dihydroxypropyl methacrylate (DHPM), 1,2-dihydroxypropyl 4-vinylbenzyl ether (DHPVB), and N-[3-(trimethoxysilyl)propyl]ethylenediamine (TMSED). Preferably, polyamine silane derivatives, in addition to capping agent cross-linkable polyelectrolytes, can be used. Polyelectrolyte capping layers can also be varied to include BPEI and other amine-bearing polyelectrolytes, such as N-[3-(trimethoxysilyl)-propyl]ethylenediamine (TMSED, hydrolyzed and crosslinked via siloxane bond formation after deposition).

Aqueous, pH 8.6 1,3-bis[tris(hydroxymethyl)methylamino]propane (BTP) buffer is a preferred rinsing agent and component of BPEI solution used to coat a previously deposited layer of OPH enzyme. Note that use of a water rinse after deposition of an OPH layer followed by attempted deposition of a BPEI layer using an aqueous BPEI solution not containing BTP buffer, leads to extraction of a portion of the previously deposited OPH enzyme from the substrate and results in poor quality multilayer films having low catalytic activities. The reason for this loss of OPH enzyme from the surface is not well understood. However, use of the BTP buffer during the rinse and as a component in the BPEI solution during deposition of the BPEI layer capping the OPH enzyme layer minimizes OPH extraction from the surface. Apparently the BTP interacts with the immobilized OPH enzyme to increase its adhesion to the underlying BPEI layer in the film. The same phenomenon can be applied to other enzymes, but with differing intensity in BTP enzyme affinity.

In contrast, attempts to deposit an OPH enzyme layer onto a BPEI layer that had been deposited from a BPEI solution containing BTP buffer and rinsed with pure BTP buffer does not lead to deposition of large amounts of OPH reproducibly. OPH is most reproducibly deposited onto a BPEI layer that has been deposited from an aqueous solution of BPEI not containing BTP buffer. Once again, the reason for this is not well understood. Therefore, to deposit a multilayer film bearing more than one OPH enzyme layer, one cannot use the capping layer of BPEI, deposited from BPEI solution containing BTP buffer, over the previous OPH as a base layer for direct deposition of the next OPH layer. Instead, one can first apply an intervening PSS layer on top of the BPEI layer capping the previous layer of OPH. One can then use the PSS layer as a base layer to apply another BPEI layer using an aqueous BPEI solution not containing the BTP buffer. In this manner, another layer of OPH enzyme may then be readily and reproducibly added to the growing multilayer film. Consequently, one such preferred processing scheme for the successful fabrication of polyelectrolyte-OPH enzyme multilayer films is shown in FIG. 1.

Processing is versatile. Woven textiles and fabrics may be used directly as substrates for deposition of the catalytic multilayer films. Alternatively, the multilayers may be deposited onto threads, which may be subsequently woven into fabrics of the desired shape. The enzyme capping layers provide sufficient protection to the underlying enzyme layer(s) such that the degree of abrasion and wear that the multilayer coated thread experiences during the weaving process is not sufficient to eliminate the catalytic activity of the resulting woven cloth.

Optionally, the top layer can be designed to kill bacteria and viruses. For example, by modifying the top layer BPEI amine with a hexyl group and quaternizing with methyl bromide, the top layer will be a bactericidal layer. See J. Lin, S. Qiu, K. Lewis, A. M. Klibanov, "Bactericidal Properties of Flat Surfaces and Nanoparticles Derivatized with Alkylated Polyethylenimines," *Biotechnol. Prog.*, 18, 1082-1086 (2002), the entire contents of which are incorporated herein by reference.

Having described the invention, the following examples are presented to illustrate specific applications of the invention, including the best mode currently known to perform the invention. It is understood that these specific examples are not intended to limit the scope of the invention described in this application.

EXAMPLES

General Considerations

Materials: All chemicals used were A.C.S. reagent grade or better from Sigma-Aldrich Chemical Co. and were used as received unless otherwise noted. Deionized water (18 MΩ-cm resistivity) was used for all experiments. Nitrogen gas for drying samples from liquid $N_2$ boil-off was passed through a 0.2 μm PTFE filter prior to use. β-cyclodextrin was obtained from Cargill Cerestar Inc. Branched polyethylenimine (BPEI) (CAS No. 25987-06-8) was a 50% wt. solution in water (Aldrich Chemical Co., catalog no. 181978, batch no. 16104HA) with $M_n$ (GPC) ~60000 g/mole and $M_w$ (LS) ~75000 g/mole. Poly(sodium 4-styrensulfonate) (PSS) (Aldrich Chemical Co., catalog no. 24,305-1, Lot no. 20025CU, CAS No. 25704-18-1) had $M_w$~70000 g/mole. Organophosphorous hydrolase (OPH) (EC 3.1.8.1) enzyme was received as freeze dried powder from Aberdeen Proving Grounds, MD, and stored in the refrigerator at 4° C. until needed for experiments. The amount of OPH enzyme was determined by estimating the total protein content and performing an enzyme assay on the samples (Y. Lee, I. Stanish, V. Rastogi, T. Cheng, and A. Singh, "Sustained Enzyme Activity of Organophosphorus Hydrolase in Polymer Encased Multilayer Assemblies," *Langmuir*, 19, 1330-1336 (2003), the entire contents of which are incorporated herein by reference). OPH enzyme samples used in our studies were technical grade (5% enzyme mixed with ~95% of trehalose along with small amounts of non-enzymatic protein). Lint-free clean room paper towels (Model 8025 Clean Room Wipes) were obtained from Liberty Industries, Inc. A clean 100% cotton undershirt (Hanes Inc.) provided cotton cloth samples. Cotton thread was 100% cotton Mouliné Spécial DMC 25 from DMC S. A., F5579 Paris cedex 12, France. Fiberglass woven cloth was style #106 from Hexcel Schwebel (piece #6493106201; sample #3664). This material had a plain weave style, a wrap count of 56, a fill count of 56, a fabric thickness of 0.04 mm, and a breaking strength of 45 lb·f/in.

Solutions: Stock aqueous solutions were prepared as described below. Polymer and buffer solutions were stable for at least two weeks following preparation. OPH enzyme solutions and $CoCl_2$ cofactor solutions were prepared fresh daily as needed. The stock solutions included:

1. BTP: This buffer was prepared as a 0.01 M solution by dissolving 2.823 g Bis-tris propane (i.e., 1,3-bis[tris(hydroxymethyl)methylamino]propane) in ~950 mL water in a 1 L volumetric flask. A 0.1 M HCl(aq) solution was then added dropwise to bring the BTP solution to pH 8.6, followed by dilution with water to 1 L in the volumetric flask and mixing.

2. CHES-w: This pH 8.6 buffer solution was prepared as a 0.01 M solution by dissolving 2.07 grams of 2-[N-Cyclohexylamino]ethanesulfonic acid in a 1 L volumetric flask containing ~900 mL water. A sufficient volume of 1 M NaOH(aq) solution was added dropwise to adjust the solution pH to 8.6 followed by the addition of water to make up volume to 1000 mL.

3. CHES-m: CHES-m buffer (0.008 M, in 20% methanol) was prepared by pipetting 200 mL methanol into a 1 L volumetric flask and mixing it with CHES-w buffer to make 1 L volume.

4. BPEI-w: A 1.5 g sample of BPEI was added to a 200 mL portion of deionized water with magnetic stirring and diluted to make a 1 L solution. The pH of the solution was adjusted to 8.6 by addition of small volumes of 2% HCl solution in water.

5. BPEI-b: This polymer solution was prepared by placing 600 mg of BPEI solution into a 250 mL beaker and adding 100 mL BTP buffer with magnetic stirring. The volume was then made up to 500 mL by adding additional volume of BTP buffer. The pH of the solution was 8.6.

6. PSS-w: A 1.03 g portion of PSS was dissolved in 1 L water to make a 0.005 M solution. This solution resulted in a pH of 6.6.

7. Stock MPT: A 26.2 mg (100 µmole) portion of methyl parathion (MPT) (MW=263.22 g/mole) was placed in a 1 L volumetric flask and 200 mL of methanol was added by pipet. CHES-w buffer was slowly added in ~50 mL aliquots with thorough mixing until the total volume of solution was 1 L. The solution was mixed and transferred to polyethylene containers, which were stored in the refrigerator at 4° C. to inhibit decomposition until needed for experiments. The MPT concentration of this solution was 100 µM, and the solution had pH ~8.6.

8. Stock PNP: A 13.9 mg (100 µmole) portion of p-nitrophenol (PNP) (MW=139.1 g/mole) was placed in a 1 L volumetric flask and 200 mL of methanol was added by pipet. CHES-w buffer was slowly added in ~50 mL aliquots with thorough mixing until the total volume of solution was 1 L. The solutions was mixed and transferred to polyethylene containers, which were stored in the refrigerator at 4° C. until needed for experiments. The PNP concentration of this solution was 100 µM and the solution had pH ~8.6.

9. Stock Co: This co-factor solution was prepared by dissolving ~1.2 mg (5 µmole) $CoCl_2 \cdot 6H_2O$ (MW=237.93 g/mole) in ~40 mL BTP in a 50 mL volumetric flask, diluting to the 50 mL mark with BTP, and mixing. The solution contains ~100 µM Co(II) in ~0.01 M BTP at pH ~8.6. This solution is prepared fresh as needed.

10. Stock OPH: This enzyme solution is prepared by dissolving ~4 mg OPH enzyme in 16 mL of freshly prepared Stock Co solution. This solution was prepared fresh each time. This solution was placed in the refrigerator (4° C.) between each deposition cycle to avoid enzyme inactivation.

Substrate Preparation and Cleaning: Cotton cloth samples were cut from the undershirt and cotton string samples were cut from the thread using scissors as needed. Both the cotton cloth and cotton thread were used directly in experiments without further cleaning. Fiberglass cloth was cut into a size appropriate for each experiment with scissors and the edges were fused by melting in a propane-air flame to prevent unraveling of the weave during subsequent handling. Fiberglass cloth samples were cleaned by a two-step process, hereafter referred to as the Standard Cleaning Protocol, prior to use. The fiberglass cloth was first immersed in a solution comprising a 1:1 v/v mixture of concentrated hydrochloric acid in methanol in a fume hood for ~1 hour. The sample was stirred with a glass-stirring rod periodically to dislodge any gas bubbles trapped on the weave. The fiberglass cloth was then rinsed thoroughly by immersion in separate containers of water at least 4 times. It was next immersed in concentrated sulfuric acid for ~1 hour. A clean glass-stirring rod was again used to dislodge any bubbles trapped in the weave. (Fiberglass cloth samples could be readily stored for at least 4 days in this cleaning bath without contamination.) The fiberglass cloth sample was then removed from the sulfuric acid and washed thoroughly with water as described for the HCl/methanol treatment. The sample was removed from the final water rinse and placed on a lint-free clean room paper towel (Model 8025 Clean Room Wiper; Liberty Industries, Inc.). The sample was stretched out flat on the towel by hand, covered with a second lint-free towel, and pressed to adsorb most of the water from the fiberglass cloth. Powder-free latex gloves were worn during this process to prevent contamination of the fiberglass cloth by oils from the bare hand. Residual moisture was removed from the fiberglass cloth using the stream of $N_2$ gas filtered through a 0.22 µm PTFE filter. The dried, clean fiberglass cloths were used immediately for coating experiments as described in subsequent examples to avoid contamination. Clean fiberglass cloth samples for use in experiments scheduled later in the same day were stored immersed in the final water rinse until needed.

General Method for Multilayer Fabrication: This section outlines the general protocol for deposition of the polyelectrolyte and enzyme multilayers onto cloth substrates. In general, polyelectrolyte multilayers containing encapsulated enzymes were prepared by sequential treatment of fiberglass cloth or cotton cloth substrates with appropriate polyelectrolyte solutions and enzyme solutions using dipping, spraying, or spin coating methods. The enzyme layers were applied by replacement of anionic polyelectrolyte layers by enzymes during the deposition process. Therefore, in general, the substrate was first coated with a cationic polyelectrolyte layer. Thereafter, alternating layers of negatively charged and positively charged polyelectrolytes were coated onto the first cationic polyelectrolyte layer. The enzyme was immobilized by replacement of anionic polyelectrolyte solution by the enzyme solution during the deposition process. Following deposition of each polyelectrolyte and enzyme layer, the substrate was washed using water or BTP buffer to remove loosely adsorbed material prior to deposition of the next layer of the multilayer film. In all cases, each enzyme layer was deposited onto and capped by an adsorbed layer of cationic polyelectrolytes to encapsulate the enzyme in the multilayer film. After completion of the multilayer fabrication process, samples were subjected to a Standard Drying Protocol involving placement in a lyophilizer and drying under vacuum (1.3-1.5 μbar) for 2 hours. Samples were then stored in a refrigerator (4° C.) until needed for experiments. In general, samples were used the day after preparation unless noted otherwise. Specific treatment sequences are described in the examples that follow. FIG. 1 shows one example of a protocol for fabrication of the film with specific conditions noted.

Standard Enzyme Activity Assay: The activity of the encapsulated enzymes in the multilayer films was tested via hydrolysis of methyl parathion (MPT) to paranitrophenol (PNP). An extinction coefficient of 9300 L·mole$^{-1}$ cm$^{-1}$ at 275 nm was first determined for MPT by appropriate dilution of the Stock MPT solution with CHES-m buffer. A series of dilutions of the Stock MPT solution with CHES-m buffer was then performed and the absorbance of each solution was measured at 275 nm in a 1.00 cm pathlength cell. A linear calibration curve of absorbance, $A_{275}$, vs. [MPT] (in μM) was then constructed. The calibration curve was described by equation (1):

$$A_{275}=0.0093 \cdot [MPT] \quad r^2=0.9999 \quad (1)$$

The analysis of PNP was performed in a more strongly basic solution to maximize the concentration of the strongly absorbing paranitrophenolate anion species. A series of dilutions of the Stock PNP solution were made using the CHES-m buffer to prepare a calibration curve. A 600 μL aliquot of each diluted PNP solution was separately mixed with a 900 μL aliquot of freshly prepared 1 mM NaOH(aq) solution (i.e., dilution factor=2.5) and the absorbance was measured at 405 nm in a 1.00 cm pathlength cell. An extinction coefficient of 14,000 L·mole$^{-1}$ cm$^{-1}$ was measured for the PNP anion. A linear calibration curve, corrected for the 2.5 dilution factor, described by equation (2) was obtained:

$$A_{405}=0.0140 \cdot [PNP] \quad r^2=0.9998 \quad (2)$$

The analysis of the activity of the encapsulated enzymes in the multilayer films was carried out by immersing the substrate coated by the polyelectrolyte-enzyme multilayer film in a beaker containing 100 mL of stirred Stock MPT solution. At various times afterwards, 600 μL aliquots of the MPT solution were withdrawn, diluted with 900 μL of freshly prepared 1 mM NaOH(aq) solution, and mixed. The absorbance of the paranitrophenolate anion was measured at 405 nm and the [PNP] was determined from the calibration curve. Plots of [PNP] vs. immersion time were constructed to map the activity of the polyelectrolyte-enzyme multilayer film cloth samples.

Standard Enzyme Binding Assay: Protein assays were carried out to determine the quantity of OPH bound in multilayer assemblies on various fabric substrates described in subsequent examples according to the literature method (Y. Lee, I. Stanish, V. Rastogi, T. Cheng, A. Singh, "Sustained Enzyme Activity of Organophosphorus Hydrolase in Polymer Encased Multilayer Assemblies," Langmuir, 19, 1330-1336 (2003), the entire contents of which is incorporated herein by reference). Briefly, a sample (~100 mg) of fabric coated with an OPH-polyelectrolyte multilayer assembly was digested with agitation for ~2 hours in 1.5 mL of a 2 M NaCl(aq) solution and then centrifuged at 5000 rpm for 3 minutes. Aliquots of Biuret reagent (2.2 mL) and Folin and Ciocalteu's phenol reagent (0.1 mL) were added to a 0.2 mL aliquot of the supernatant isolated during centrifugation and the absorbance of the resulting solution at 720 nm was measured. Protein content was calculated by comparison to standard curves prepared using known concentrations of OPH. Hereafter, this method will be referred to as the Standard Enzyme Binding Assay.

Example 1

Fabrication of Polyelectrolyte-OPH Enzyme Multilayer on Fiberglass Cloth by Dip Coating This example demonstrates the preparation of a polyelectrolyte-enzyme multilayer containing a single layer of the OPH enzyme on a woven fiberglass cloth sample by the dip coating method.

Two circular samples of fiberglass cloth of ~3 inch diameter each were cut from the roll of cloth obtained from the supplier (Hexcel) and cleaned using the Standard Cleaning Protocol. Separate plastic cylindrical 50 mL centrifuge tubes (Falcon BD), each of length ~4.5 inches, were used to secure the samples. The centrifuge tube diameter was constant at ~1.25 inches over a 4 inch length of the tube, rapidly tapering to ~0.25 inches at the bottom of the tube. Each tube was prepared for use by drilling a hole through the 0.25 inch diameter plastic section of the bottom of the tube to equalize air pressure and permit free flow of solution into and out of the tube during sample treatment. The freshly cleaned fiberglass cloths were stretched tightly by hand over the threaded mouths of the centrifuge tubes and secured with rubber bands. Excess fiberglass cloth was trimmed away using scissors or a razor blade until flush with the rubber band and discarded. Each centrifuge tube, affixed with the sample cloth, was mounted vertically with the vent hole facing upwards using a standard laboratory clamp. A 250 mL beaker containing a Teflon® stirbar was placed on a magnetic stirrer immediately under each mounted sample. An aliquot of BPEI-w solution (~100 mL) was added to the beaker and stirring was begun. Each centrifuge tube bearing the sample cloth was then lowered into the stirred solution until all portions of the fiberglass cloth were immersed and left for 10 minutes. The tubes were then removed from the BPEI-w solution, unclamped, and gently shaken to remove adherent BPEI-w solution. A beaker containing 100 mL of stirred water was placed on the stirring plate and the tubes were returned to the clamp and lowered into the rinse water until each fiberglass cloth was again completely immersed. After 1 minute the tubes were removed from the rinse water, unclamped, and again gently shaken to remove excess solvent. The sample cloth on the first tube was designated as a control cloth. It was dried further using a stream of filtered nitrogen gas, subjected to the Standard Drying Protocol, and stored in the refrigerator until needed for further experiments.

After removal from the aqueous rinse solution, the tube bearing the second cloth was again clamped and immersed in a beaker containing stirred Stock OPH solution, which had been allowed to warm to room temperature after removal from storage in the refrigerator. Care was taken to ensure that the entire cloth sample was immersed. After 10 minutes, the tube was withdrawn from the OPH solution, unclamped, and again shaken to remove excess solution. The tube was remounted in the clamp and the sample cloth immersed in a stirred BTP buffer solution for 2 minutes. Following the rinse with BTP buffer, the tube was unclamped, shaken to remove excess buffer from the sample cloth, and remounted in the clamp. The tube was then lowered into a stirred BPEI-b solution to deposit a capping layer of the BPEI polymer over the OPH enzyme layer on the immersed sample cloth. After 10 minutes, the tube was removed from the BPEI-b solution, unclamped, and shaken to remove excess BPEI-b solution. The tube was then returned to the clamp and the sample cloth immersed in stirred BTP solution for 1 minute as a final washing cycle. The tube was removed from the BTP buffer wash solution, unclamped, and gently shaken to remove excess BTP buffer solution. The sample cloth was blown dry using a filtered nitrogen gas stream and separated from the tube by cutting the rubber band. The treated sample cloth was transferred to the lyophilizer for drying using the Standard Drying Protocol. Dried sample cloths were then stored in the refrigerator until needed for experiments.

The multilayer film structure of the treated sample cloth is conveniently represented by the notation, FG/BPEI/OPH/BPEI, where FG represents the underlying fiberglass cloth substrate coating sequentially by layers of BPEI polyelectrolyte, OPH enzyme, and a capping layer of BPEI polyelectrolyte. The corresponding notation for the control fiberglass cloth is FG/BPEI. After the multilayer fabrication process was completed a 500 µL aliquot of the Stock OPH used in the deposition was analyzed to confirm enzyme activity using the Standard Enzyme Activity Assay. OPH activity of the used solution was identical within experimental error (±5%) to that of the fresh enzyme solution.

Example 2

MPT Hydrolysis Activity of Multilayer-coated Fiberglass Cloth Containing a Single OPH Enzyme Layer Prepared by Dip Coating This example demonstrates that fiberglass cloth dip coated with a multilayer polyelectrolyte film encapsulating a single layer of OPH enzyme is capable of hydrolyzing MPT in solution to Pnp.

The control FG/BPEI (weight 80 mg) and sample FG/BPEI/OPH/BPEI cloths (weight 82 mg) prepared in Example 1 were removed from the refrigerator and allowed to warm to room temperature. Each cloth was then fully immersed in a separate beaker containing 100 mL of stirred Stock MPT solution for 22 hours at room temperature (23±2° C.). The clear and colorless MPT solution containing the FG/BPEI/OPH/BPEI sample cloth developed a clear yellow color with increasing time. Little, if any, color was observed in the MPT solution containing the FG/BPEI control cloth. The sample and control cloths were then removed from the MPT solutions, rinsed carefully, blown dry with the filter nitrogen gas stream, and returned to storage in the refrigerator. The Standard Enzyme Activity Assay was performed for each of the MPT solutions. The assay indicated that only ~0.8 µM PNP was produced in the solution exposed to the FG/BPEI control cloth, consistent with negligible MPT hydrolysis. In contrast, ~18 µM PNP was detected in the MPT solution treated using the FG/BPEI/OPH/BPEI sample cloth, demonstrating the retained activity of the encapsulated OPH enzyme towards MPT hydrolysis in this sample.

Example 3

Reproducibility of Fabrication and Hydrolytic Activity of Multilayer-coated Fiberglass Cloth Containing a Single OPH Enzyme Layer Prepared by Dip Coating This experiment illustrates the degree with which the multilayer-coated fiberglass cloths having MPT hydrolysis activity can be fabricated by the dip coating method.

The fabrication procedure described in Example 1 was repeated 3 times using fresh samples of fiberglass cloth in each case. Fresh solutions were used to coat the samples with encapsulated OPH enzyme towards hydrolysis of MPT as described in example 2. Once again, the 3 FG/BPEI control clothes produced only ~0.8 µM PNP in each case, indicating negligible hydrolysis of the MPT solution. The separately prepared FG/BPEI/OPH/BPEI sample cloths produced ~15 µM PNP, ~16 µM PNP, and ~15 µM PNP in good agreement with the 18 µM PNP produced using the corresponding sample from Example 2. The average activity exhibited by the 4 sample cloths of Examples 2 and 3 is 16 µM PNP with a standard deviation ($\sigma$) of ±1.2 µM PNP, suggesting a reproducibility ($2\sigma$) of ~15% for the fabrication and hydrolysis processes.

Example 4

Fabrication of Multilayer-coated Fiberglass Cloth Containing Multiple OPH Enzyme Layers by Dip Coating This example describes the preparation of fiberglass cloths coated by multilayer films bearing more than one layer of enzyme. The example shows the fabrication of a film containing 4 layers of the OPH enzyme.

A sample of fiberglass cloth bearing a single layer of OPH enzyme was fabricated as described in Example 1 using fresh OPH solution. However, following binding of the capping BPEI-b layer and subsequent rinse in the BTP solution, treatment was continued by immersion for 10 minutes in a stirred PSS-w solution. The sample was then gently shaken to remove excess PSS solution, rinsed for 1 minute in stirred water, and gently shaken to remove excess rinse water. The treatment sequence of Example 1 was repeated to apply the next BPEI-w layer, the second OPH layer, and the next BPEI-b layer. Following application of a second PSS-w layer and an aqueous rinse, the treatment sequence of Example 1 was again performed to apply the third BPEI-w, OPH, and BPEI-b layers. Another layer of PSS-w was then applied and the sample rinsed in water as described above. The sample was then subjected to a final treatment sequence as described in Example 1 to apply the fourth layers of BPEI-w, OPH, and BPEI-b. The multilayer sequence of treated sample cloth is FG/(BPEI/OPH/BPEI/PSS)$_3$/BPEI/OPH/BPEI. In general, a multilayer containing "x" layers of OPH can be prepared through repetition of the treatment sequence of Example 1 "x" times, using a PSS layer as a separation polyelectrolyte layer between each repetition of the treatment sequence of Example 1.

Example 5

MPT Hydrolysis Activity of Multilayer-coated Fiberglass Cloth Containing Multiple OPH Enzyme Layers Prepared by Dip Coating This example demonstrates that fiberglass cloth coated with a multilayer polyelectrolyte film encapsulating 4 layers of OPH enzyme is capable of hydrolyzing MPT in solution to PNP.

The ability of the sample cloth fabricated in Example 4 having the multilayer film structure FG/(BPEI/OPH/BPEI/PSS)$_3$/BPEI/OPH/BPEI to hydrolyze MPT solution was tested using the procedure described in Example 2. A freshly prepared control cloth having the structure FG/BPEI was also tested. The control cloth produced ~0.8 μM PNP, in agreement with our observations in Examples 2 and 3. The sample cloth containing 4 layers of OPH enzyme produced ~31 μM PNP, a value about twice that observed for the sample cloths containing a single layer of OPH enzyme in Examples 2 and 3. Consequently, sample cloths containing multiple enzyme layers are capable of hydrolyzing MPT in solution and can do so at a greater rate than cloths bearing only a single OPH enzyme layer in their multilayer coatings.

Example 6

Time Dependence of the MPT Hydrolysis Activity of Multilayer Fiberglass Cloths Bearing a Single OPH Enzyme Layer Prepared by Dip Coating This example illustrates the activity of a sample cloth bearing a single OPH enzyme layer towards the repetitive hydrolysis of MPT in solution as a function of time since fabrication.

The fiberglass sample cloth (weight ~80 mg) fabricated in Example 1 having the multilayer structure FG/BPEI/OPH/BPEI was used for this test. This sample cloth was used to sequentially hydrolyze fresh 100 mL aliquots of Stock MPT solution as described in Example 2 during a ~17 day time period. Four separate MPT solutions were hydrolyzed during the 5 working days in each week. Following each hydrolysis experiment, the sample cloth was rinsed with water for ~1 minute and blown dry with a filtered stream of nitrogen gas before being used for the next experiment. The Standard Enzyme Activity Assay was used to measure the quantity of PNP produced in each MPT solution immediately after completion of each 22 hour experiment. On Fridays and during the weekends, no hydrolysis experiments were conducted and the sample cloth remained in storage in the refrigerator. The activity assay data is illustrated as a function of the number of hydrolysis cycles and age of the sample cloth in Table 1.

TABLE 1

Reuse of Fiberglass Sample Cloth Bearing a Single OPH Layer for MPT Hydrolysis

| [PNP] Produced (μM) | 18 | 17 | 13 | 12 | 15 | 7 | 9 | 9 | 15 | 6 | 5 | 8 |
|---|---|---|---|---|---|---|---|---|---|---|---|---|
| Sample Age (Days) | 0 | 1 | 2 | 3 | 7 | 8 | 9 | 10 | 14 | 15 | 16 | 17 |
| Hydrolysis Cycle Number | 1 | 2 | 3 | 4 | 5 | 6 | 7 | 8 | 9 | 10 | 11 | 12 |

In general, the data indicate that the activity of the sample cloth towards hydrolysis of MPT decreases with the age and use of the sample cloth, with the sample reaching a value of ~25-35% of its initial hydrolysis activity after ~17 days of use. Consequently, the sample cloth retains measurable activity for the hydrolysis of MPT for at least a 17 day period of repeated use. Hydrolysis cycle number 5 and 9 represent experiments begun on the Monday of the work week following storage of the sample in the refrigerator over the weekend. These data indicate that samples temporarily regain a portion of their lost catalytic activity towards solution phase hydrolysis of MPT upon storage for ~3 days in the refrigerator during the 17 day time period covered by these experiments.

Example 7

Time Dependence of the MPT Hydrolysis Activity of Multilayer Fiberglass Cloths Bearing 4 OPH Enzyme Layers Prepared by Dip Coating This example illustrates the activity of a sample cloth bearing 4 OPH enzyme layers towards the repetitive hydrolysis of MPT in solution as a function of time since fabrication.

The fiberglass sample cloth (weight ~82 mg) fabricated in Example 4 having the multilayer structure FG/(BPEI/OPH/BPEI/PSS)$_3$/BPEI/OPH/BPEI was used for this test. This sample cloth was used to sequentially hydrolyze fresh 100 mL aliquots of Stock MPT solution as described in Example 2 during a ~20 day time period. Separate, fresh MPT solutions were hydrolyzed each day that an experiment was run. Following each hydrolysis experiment, the sample cloth was rinsed with water for ~1 minute and blown dry with a filtered stream of nitrogen gas before use in the next experiment. The Standard Enzyme Activity Assay was used to measure the quantity of PNP produced in each MPT solution immediately after completion of each 22-hour experiment. During the weekends, no hydrolysis experiments were conducted and the sample cloth remained in storage in the refrigerator. Representative activity assay data is illustrated as a function of the number of hydrolysis cycles of the sample cloth in Table 2.

TABLE 2

Reuse of Fiberglass Sample Cloth Bearing 4 OPH Layers for MPT Hydrolysis

| [PNP] Produced (μM) | 31 | 14 | 22 | 20 | 21 | 24 | 20 | 19 | 22 | 23 |
|---|---|---|---|---|---|---|---|---|---|---|
| Sample Age (Days) | 0 | 1 | 2 | 3 | 8 | 9 | 10 | 14 | 17 | 20 |
| Hydrolysis Cycle Number | 1 | 2 | 3 | 4 | 5 | 6 | 7 | 8 | 9 | 10 |

The fifth hydrolysis cycle was performed following a long holiday weekend in which the sample had been refrigerated for ~5 days. The eighth hydrolysis cycle was performed after a three-day refrigeration over a weekend. The sample was also stored in the refrigerator for ~2 days following each of the eighth and ninth hydrolysis cycles. The results in Table 2 clearly indicate that hydrolysis of MPT continues to occur at measurable rates for the sample bearing 4 OPH enzyme layers for extended periods after fabrication of the sample.

Example 8

Fabrication of Multilayer-coated Fiberglass Cloth Bearing a Single Layer of OPH Enzyme by Spray Coating This example describes the fabrication of a multilayer coating containing one layer of OPH enzyme on a fiberglass cloth using a spray coating method.

A plastic drink cup (32 U.S. ounce capacity; ~4 inch diameter×5 inch height) having a rim at its mouth with a corresponding plastic lid capable of being secured to said cup when said lid is snapped over said rim was modified as a sample holder for this experiment. A circular hole of ~2.5 inch diameter, concentric with the center of the circular lid, was cut from said lid. The bottom of the plastic cup was next cut away, leaving an approximately cylindrical structure of diameter ~4 inches and height ~4 inches that was open at both ends. A ~5 inch diameter piece of fiberglass cloth was cleaned using the Standard Cleaning Process and stretched taut over the mouth of the plastic cup. The fiberglass cloth was secured to the cup by snapping the lid onto the mouth of the cup over the stretched, taut, fiberglass cloth. In this manner, a circular area of fiberglass cloth ~2.5 inches in diameter was exposed in the area of the lid that had been cut away and was available for spraying treatments. Excess cloth protruding from the lid along the rim of the cup was trimmed back to the rim with scissors or a razor blade. The trimmings were discarded.

A cardboard box of dimensions 16 inch height×12 inch width×10 inch depth was placed in the fume hood to act as a catch basin for aerosols during spraying such that one of the 16 inch×12 inch sides faced the experimenter and a 12 inch×10 inch side comprised the top of the box. The top of the box and the front face of the box were cut away and discarded. A second cup, identical to the first and not modified in any way, was obtained to act as a solution catch basin during spraying. This second cup was mounted in an iron ring clamp inside the cardboard box in the fume hood such that the mouth of the cup was tilted ~45° from the vertical and faced the experimenter. The assembly comprising the fiberglass cloth sample secured to the first (bottomless) cup by the modified lid was then nested in the second cup mounted in the iron ring clamp in the hood.

Solutions of BPEI-w, BTP, and BPEI-b were freshly prepared and directly loaded into separate Nalgene® aerosol spray bottles (Aldrich Chemical Co., catalog no. Z27, 925-0). Stock OPH solution was filtered using a 0.2 µm PTFE filter attached to a 5 mL plastic Fortuna® syringe to eliminate any insoluble particulates that could clog the tiny outlet of the spray bottle atomizer during the spraying process prior to loading into another spray bottle. Each solution was prepared for spraying by pressurizing the appropriate spray bottle using a detachable hand pump. The pump was depressed 20 times to charge the sprayer. The solution was then sprayed onto the fiberglass cloth sample by positioning the spray bottle ~4-6 inches from the surface of the fiberglass cloth such that the bottle was parallel to the surface of the fiberglass cloth and the nozzle directly faced the fiberglass cloth. The solution was sprayed by depressing the nozzle continuously for ~10-12 seconds. The spray bottle was depressurized after each use and re-pressurized as described above when needed again to ensure equal pressure for delivery of the spray during each deposition cycle.

In general, the multilayer films were fabricated on the fiberglass cloth sample by spraying the appropriate polyelectrolyte solution or filtered Stock OPH solution onto the cloth for 10-12 seconds, allowing the sample to stand undisturbed for 2 minutes, and spraying the sample 10-12 seconds with the appropriate rinse solution (i.e., water or BTP buffer). The assembly comprising the fiberglass cloth sample secured to the first (bottomless) cup by the modified cup lid was then removed from the second solution catch basin cup and gently shaken to remove excess liquid from the sample cloth. Said assembly was placed back into said second cup and the process repeated using the appropriate solution to deposit the next layer of polyelectrolyte on OPH enzyme. In order to fabricate the multilayer film bearing a single OPH enzyme layer, the cloth was first sprayed with the BPEI-w solution and then sprayed with water for rinsing. The second cycle deposited the enzyme by spraying with the filtered stock enzyme solution, followed by spraying with the BTP buffer solution for rinsing. The final polyelectrolyte-capping layer was then applied in the third spraying cycle. BPEI-b solution was sprayed onto the sample cloth, followed by spraying the BTP buffer solution for rinsing.

After this final rinse with BTP buffer, the assembly comprising the fiberglass cloth secured to the first (bottomless) cup by the modified plastic lid was removed from the second cup. The modified lid securing the treated fiberglass sample to the first (bottomless) cup was removed to free the cloth. The area of the cloth exposed directly to the sprays during treatment was cut from the remaining cloth using scissors. This portion of treated cloth was placed with the sprayed side facing up on a lint-free clean room paper towel for ~5 minutes to enhance drying of the sample. The treated fiberglass sample cloth was then transferred to the lyophilizer and subjected to the Standard Drying Protocol before being stored in the refrigerator.

Example 9

Fabrication of Multilayer-Coated Fiberglass Cloth Bearing Multiple Layers of OPH Enzyme by Spray Coating This example extends the method of Example 8 for the fabrication of multilayer-coated fiberglass cloths bearing 3 OPH enzyme layers.

A sample of fiberglass cloth bearing a single layer of OPH enzyme was fabricated by spray coating as described in Example 8. However, following binding of the capping BPEI-b layer and subsequent rinse in the BTP solution, treatment was continued by spraying 10-12 seconds with PSS-w solution. The sample was allowed to stand for 2 minutes and then sprayed 10-12 seconds using rinse water. The assembly comprising the cloth sample secured to the first (bottomless) cup using the modified lid was removed from the second cup and shaken to dislodge excess liquid. The assembly was replaced into the second cup and the spray treatment sequence of Example 8 was repeated to apply the next BPEI-w layer, the second OPH layer, and the next BPEI-b layer. Following spray application of a second PSS-w layer and an aqueous rinse, the treatment sequence of Example 8 was again performed to apply the third BPEI-w, OPH, and BPEI-b layers. The multilayer sequence of treated sample cloth is FG/(BPEI/OPH/BPEI/PSS)$_2$/BPEI/OPH/BPEI. In general, a multilayer containing "x" layers of OPH can be prepared through repetition of the spray treatment sequence of Example 8 "x" times, using a PSS layer as a separation polyelectrolyte layer between each repetition of the treatment sequence of Example 8.

Example 10

Fabrication of Multilayer-coated Fiberglass Cloth Bearing a Single Layer of OPH Enzyme by Spin Coating This example illustrates the fabrication of a multilayer-coated fiberglass cloth bearing a single layer of OPH enzyme using a spin coating method.

A ~3.50 inch diameter piece of fiberglass cloth was cleaned using the Standard Cleaning Process and stretched taut over a 3 inch diameter silicon wafer. The fiberglass cloth was secured to the silicon wafer using Mini Binder Clips (Charles Leonard Inc., Catalog No. 50001, 9/16 inch size, 1/4 inch capacity) of the type used in place of staples to secure stacks of papers. The clips were mounted uniformly (equidistant) around the circumference of the wafer. The wafer bearing the secured cloth was placed centered on the 2-inch diameter wafer chuck of a SCS spin coater (Model P6204, Specialty Coating Systems Inc., Indianapolis, Ind.). Vacuum was established to the chuck and the spin coater was activated. Test runs were made by applying ~6-8 mL of water to the sample cloth and spinning the sample at various speeds for various times. Use of spinning speeds in excess of ~1600 rpm for 20-30 seconds readily removed the water from the sample, but also occasionally resulted in separation of the wafer from the chuck. It was eventually determined that spinning speeds of 1000 rpm for 20 seconds were sufficient to remove excess liquid from the sample cloth without separation of the wafer from the sample chuck. Consequently, these conditions were used during the treatment of the sample cloth with various polyelectrolyte, enzyme, and rinse solutions as described below.

In general, coating of the fiberglass sample cloth was accomplished by puddling ~4-6 mL of the appropriate polyelectrolyte, enzyme, or rinse solution (i.e., water or BTP buffer) onto the sample cloth, allowing the solution to stand on the cloth for a short time (i.e., 2 minutes for polyelectrolyte or Stock OPH solutions and 30 seconds for rinse solutions), and removing the excess solution by activating the spin coater for 20 seconds at 1000 rpm. The process was repeated until all depositions and rinses were completed. For the fabrication of a multilayer-coated fiberglass cloth bearing a single OPH enzyme layer, the fiberglass cloth was first treated with BPEI-w solution, spun dry, rinsed with water, and spun dry again. Stock OPH enzyme solution was next applied to the fiberglass cloth, which was then spun dry, rinsed with BTP buffer solution, and spun dry again. Finally, the cloth was treated with the BPEI-b solution, spun dry, rinsed with BTP buffer solution, and spun dry again. The wafer was removed from the spin coater chuck and the Mini Binder Clamps were released to remove the treated fiberglass cloth. The edges of the cloth, which had been covered by the Mini Binder Clip or overhung the edge of the silicon wafer during the treatment process, were trimmed away with scissors and discarded. The remainder of the treated fiberglass sample cloth was subjected to the Standard Drying Protocol and stored in the refrigerator. The multilayer film deposited onto the fiberglass sample cloth has the structure FG/BPEI/OPH/BPEI.

Example 11

MPT Hydrolysis Activity of Multilayer-coated Fiberglass Cloth Containing a Single OPH Enzyme Layer Prepared by Spray Coating This example demonstrates that fiberglass cloth spray coated with a multilayer polyelectrolyte film encapsulating a single layer of OPH enzyme is capable of hydrolyzing MPT in solution to PNP.

The experiment of Example 2 was repeated using a FG/BPEI control cloth and a piece of the spray coated FG/BPEI/OPH/BPEI cloth (weight ~115 mg) prepared in Example 8. The Standard Enzyme Activity Assay indicated that only ~0.8 µM PNP was produced in the MPT solution exposed to the FG/BPEI control cloth, consistent with negligible MPT hydrolysis. In contrast, ~5.7 µM PNP was detected in the MPT solution treated using the FG/BPEI/OPH/BPEI sample cloth, demonstrating the retained activity of the encapsulated OPH enzyme towards MPT hydrolysis in this sample.

Example 12

MPT Hydrolysis Activity of Multilayer-Coated Fiberglass Cloth Containing Multiple OPH Enzyme Layers Prepared by Spray Coating This example demonstrates that fiberglass cloth spray coated with a multilayer polyelectrolyte film encapsulating 3 layers of OPH enzyme is capable of hydrolyzing MPT in solution to PNP.

The experiment of Example 2 was repeated using a FG/BPEI control cloth and a piece of the spray coated FG/(BPEI/OPH/BPEI/PSS)$_2$/BPEI/OPH/BPEI cloth (weight ~99 mg) prepared in Example 9. The Standard Enzyme Activity Assay indicated that only ~0.7 µM PNP was produced in the MPT solution exposed to the FG/BPEI control cloth, consistent with negligible MPT hydrolysis. In contrast, ~6.1 µM PNP was detected in the MPT solution treated using the FG/(BPEI/OPH/BPEI/PSS)$_2$/BPEI/OPH/BPEI sample cloth, demonstrating the retained activity of the encapsulated OPH enzyme towards MPT hydrolysis in this sample.

Example 13

MPT Hydrolysis Activity of Multilayercoated Fiberglass Cloth Containing a Single OPH Enzyme Layer Prepared by Spin Coating This example demonstrates that fiberglass cloth spin coated with a multilayer polyelectrolyte film encapsulating a single layer of OPH enzyme is capable of hydrolyzing MPT in solution to PNP.

The experiment of Example 2 was repeated using a FG/BPEI control cloth and a piece of the spin coated FG/BPEI/OPH/BPEI cloth (weight ~65 mg) prepared in Example 10. The Standard Enzyme Activity Assay indicated that only ~0.7 µM PNP was produced in the MPT solution exposed to the FG/BPEI control cloth, consistent with negligible MPT hydrolysis. In contrast, 55.6 µg PNP (4 µM PNP/80 mg silica cloth) was detected in the MPT solution treated using the FG/BPEI/OPH/BPEI sample cloth, demonstrating the retained activity of the encapsulated OPH enzyme towards MPT hydrolysis in this sample.

Example 14

Fabrication of Multilayercoated Cotton Cloth Bearing a Single Layer of OPH Enzyme by Dip Coating This example demonstrates the preparation of a polyelectrolyte-enzyme multilayer containing a single layer of the OPH enzyme on a cotton cloth sample by the dip coating method.

The experiment described in Example 1 was repeated using a single cotton cloth (Hanes, Inc.), rather than the fiberglass cloth, as the substrate sample. A multilayer film of structure CC/BPEI/OPH/BPEI, where the abbreviation CC refers to the cotton cloth substrate, was deposited onto the cotton cloth. In this case, because an untreated cotton cloth serves as a suitable control, no control sample of structure CC/BPEI analogous to the FG/BPEI of Example 1 was prepared.

Example 15

MPT Hydrolysis Activity of Multilayercoated Cotton Cloth Containing a Single OPH Enzyme Layer Prepared by Dip, Coating This example shows the activity of the dip coated multilayer-coated cotton cloth of Example 14 having a single OPH enzyme layer towards the hydrolysis of MPT to PNP.

The experiment described in Example 2 was repeated using a piece of the Hanes cotton cloth as a control and the CC/BPEI/OPH/BPEI sample (weight ~83 mg) prepared in Example 14. The Standard Enzyme Activity Assay indicated that 1.1 µM was produced in the MPT solution exposed to the control cotton cloth. In contrast, ~86.5 µM PNP was produced in the MPT solution exposed to the CC/BPEI/OPH/BPEI sample, consistent with effective hydrolysis of MPT.

Example 16

Fabrication of Multilayercoated Cotton Cloth Bearing a Single Layer of OPH Enzyme by Spray Coating This example describes the fabrication of a multilayer coating containing one layer of OPH enzyme on a cotton cloth using a spray coating method.

The experiment described in Example 8 was repeated using a single cotton cloth (Hanes, Inc.), rather than the fiberglass cloth, as the substrate sample. A multilayer film of structure CC/BPEI/OPH/BPEI was deposited onto the cotton cloth. In this case, because an untreated cotton cloth serves as a suitable control, no control sample of structure CC/BPEI analogous to the FG/BPEI of Example 1 was prepared.

Example 17

MPT Hydrolysis Activity of Multilayercoated Cotton Cloth Containing a Single OPH Enzyme Layer Prepared by Spray Coating This example shows the activity of the spray coated multilayer-coated cotton cloth of Example 16 having a single OPH enzyme layer towards the hydrolysis of MPT to PNP.

The experiment described in Example 2 was repeated using a piece of the Hanes cotton cloth (89 mg) as a control and the CC/BPEI/OPH/BPEI sample (787 mg) prepared in Example 16. The Standard Enzyme Activity Assay indicated that 1.1 µM PNP was produced in the MPT solution exposed to the control cotton cloth. In contrast, ~97.1 µM PNP was produced in the MPT solution exposed to the CC/BPEI/OPH/BPEI sample, consistent with effective hydrolysis of MPT.

Example 18

Fabrication of Multilayercoated Cotton Cloth Bearing a Single Layer of OPH Enzyme by Spin Coating This example demonstrates the preparation of a polyelectrolyte-enzyme multilayer containing a single layer of the OPH enzyme on a cotton cloth sample by the spin coating method.

The experiment described in Example 10 was repeated using a single cotton cloth (Hanes, Inc.), rather than the fiberglass cloth, as the substrate sample. A multilayer film of structure CC/BPEI/OPH/BPEI was deposited onto the cotton cloth. In this case, because an untreated cotton cloth serves as a suitable control, no control sample of structure CC/BPEI analogous to the FG/BPEI of Example 1 was prepared.

Example 19

MPT Hydrolysis Activity of Multilayercoated Cotton Cloth Containing a Single OPH Enzyme Layer Prepared by Spin Coating This example shows the activity of the dip coated multilayer-coated cotton cloth of Example 18 having a single OPH enzyme layer towards the hydrolysis of MPT to PNP.

The experiment described in Example 2 was repeated using a piece of the Hanes cotton cloth (89 mg) as a control and the CC/BPEI/OPH/BPEI sample (480 mg) prepared in Example 18. The Standard Enzyme Activity Assay indicated that 1.1 µM PNP was produced in the MPT solution exposed to the control cotton cloth. In contrast, 83 µM PNP was produced in the MPT solution exposed to the CC/BPEI/OPH/BPEI sample, consistent with effective hydrolysis of MPT.

Example 20

Fabrication of Polyelectrolyte-OPH Enzyme Multilayer on Cotton Thread by Dip Coating This example demonstrates the preparation of a polyelectrolyte-enzyme multilayer containing a single layer of the OPH enzyme on a cotton thread sample by the dip coating method.

An 8-meter length of 100% cotton thread (Mouliné Spécial DMC 25, DMC S:A., F5579 Paris cedex 12, France) was placed loosely in a beaker containing a Teflon® stirbar. BPEI-w solution sufficient to cover the thread was added to the beaker and gently stirred for 15 minutes. The BPEI-w solution was decanted from the beaker and the thread was rinsed 3 times by immersion in water. The thread was allowed to stand in the final water rinse solution for 2 minutes with stirring. The thread was then removed from the beaker and pressed between two lint-free paper cleanroom towels to remove excess liquid before being returned to the empty beaker. Stock OPH solution was added to the beaker and the sample was gently stirred for 15 minutes. The enzyme solution was decanted from the beaker and subjected to the Standard Enzyme Activity Assay to verify the activity of the OPH enzyme. The thread in the beaker was immersed in BTP buffer rinse solution with gentle stirring for 2 minutes. The thread was then removed, gently pressed between two lint-free cleanroom towels as described above, and placed in a beaker containing stirred BPEI-b solution for 15 minutes. The BPEI-b solution was then decanted from the beaker and replaced with stirred BTP rinse buffer. After 2 minutes, the thread was removed from the beaker and again pressed between two lint-free cleanroom towels to remove excess liquid. The thread was then transferred to the lyophilizer and subjected to the Standard Drying Protocol. The treated thread was stored in the refrigerator until needed for experiments. The structure of the treated thread was CT/BPEI/OPH/BPEI, where the abbreviation CT refers to the cotton thread.

Example 21

MPT Hydrolysis Activity of Multilayercoated Cotton Thread Containing a Single OPH Enzyme Layer Prepared by Dip Coating This example shows the activity of the dip coated cotton thread of Example 20 having the structure CT/BPEI/OPH/BPEI towards the hydrolysis of MPT to PNP.

A 15 inch length of the multilayer-coated cotton thread from Example 20 having the structure CT/BPEI/OPH/BPEI was loosely packed into the bottom of a plastic cylindrical 50 mL centrifuge tube (Falcon BD). A 15-inch length of cotton thread, untreated by polyelectrolyte or OPH enzyme solutions, was similarly placed in a second tube. A third tube was left empty. A 2 mL aliquot of Stock MPT, which completely covered the cotton threads, was added to each tube. The tubes were capped and allowed to stand undisturbed for 6 hours at 23±2° C. After 6 hours, a Standard Enzyme Activity Assay was performed for the solution in each tube to determine the concentration of PNP produced by hydrolysis of the MPT. The [PNP] in the control tube, which did not contain any cotton thread, was 0.6 µM, indicating that the MPT solution was stable in the absence of the cotton threads. The [PNP] present in the tube containing the untreated cotton thread was 2.0 µM, consistent with minor hydrolysis of MPT by chemical residues in the thread. In contrast, 98 µM PNP was observed in the tube containing the multilayer-coated cotton thread bearing the single layer of OPH enzyme. These results indicate that OPH enzyme immobilized on the cotton thread is an effective catalyst for the hydrolysis of MPT to PNP in solution.

Example 22

MPT Hydrolysis Activity of Multilayer Woven Cotton Cloth Bearing a Single OPH Enzyme Layer Prepared by Dip Coating This example demonstrates that OPH enzyme activity towards hydrolysis of MPT to PNP in solution is maintained for the cotton threads even after they are woven into a fabric.

The multilayer-coated cotton thread from Example 20 having the structure CT/BPEI/OPH/BPEI was woven by hand into a square piece of fabric having dimensions ~5.0 cm×~1.5 cm (weight 803 mg). The sample of woven cotton fabric was placed in a plastic cylindrical 50 mL centrifuge tube (Falcon BD) and a 20 mL aliquot of fresh Stock MPT solution was added. A second fabric was woven with dimensions ~5.0 cm×~1.5 cm (weight ~945 mg) from cotton thread that had not been treated with polyelectrolyte or OPH solutions as a control. This was placed in a separate centrifuge tube containing a 20 mL aliquot of fresh Stock MPT solution. A third tube containing only the 20 mL aliquot of fresh Stock MPT solution (no cotton fabric) was also prepared. Each of the tubes was sealed, mounted to a laboratory rotator (Glascol, Terre Haute, Ind., Catalog No. 099A RD4512), and gently agitated overnight (~14 hours). A Standard Enzyme Activity Analysis was then performed on each solution. The [PNP] produced in the tube containing no cotton fabric was 1 µM, indicating that the MPT solution was stable towards extraneous decomposition during the experiment. For the sample containing the untreated control cotton fabric, ~2 µM PNP was measured consistent with the negligible hydrolysis of MPT by the cotton thread exhibited in Example 21. In contrast, [PNP] ~99 µM was measured for the fabric woven from the CT/BPEI/OPH/BPEI cotton thread, consistent with complete MPT hydrolysis during the experiment. Consequently, sufficient enzymatic activity of the OPH in the CT/BPEI/OPH/BPEI cotton thread of Example 21 is maintained during the mechanical manipulations (and potential abrasion) of the thread during the process of weaving the thread into a fabric.

Example 23

Time Dependence of the MPT Hydrolysis Activity of Multilayer Woven Cotton Cloth Bearing a Single OPH Enzyme Layer Prepared by Dip Coating This example illustrates the activity of the multilayer-coated woven cotton fabric bearing a single OPH enzyme layer of Example 22 towards the repetitive hydrolysis of MPT in solution as a function of time since fabrication.

The woven cotton fabric from Example 22 was rinsed 3 times with water and dried by pressing between two layers of lint-free cleanroom towels at the conclusion of the experiment described in Example 22. It was then transferred to another 50 mL centrifuge tube (Falcon BD) containing a fresh 20 mL aliquot of Stock MPT. The tube was capped, secured to the laboratory rotator, and again gently agitated overnight (~14 hours). Afterwards, the Standard Enzyme Activity Analysis performed on the solution showed that ~67 µM PNP had formed. The woven cotton fabric was removed from the tube, rinsed three times with water, and pressed between two lint-free cleanroom towels to remove excess liquid. It was then placed in another centrifuge tube containing a fresh 20 mL aliquot of Stock MPT solution, sealed, and gently agitated as described above overnight (~14 hours). The degree of hydrolysis of the MPT again was measured. The amount of PNP generated after this third use cycle was ~42 µM. Consequently, the cotton fabric woven from the CT/BPEI/OPH/BPEI cotton thread is capable of reuse over a several day period while maintaining sufficient catalytic activity towards the hydrolysis of MPT to PNP in solution.

Example 24

Determination of the Relative Binding Efficiencies of MPT and PNP in Polycyclodextrin Resin This example illustrates the relative binding efficiencies of MPT and PNP in a polycyclodextrin resin.

A poly-β-cyclodextrin resin was prepared by reaction of β-cyclodextrin and 1,6-diisocyanatohexane (DICH) in dimethylformamide (DMF) solution. Specifically, 25 grams (~22 mmoles) of β-cyclodextrin and 30 grams (178 mmoles) of DICH were dissolved in 700 mL of DMF. The solution was heated with stirring to 90-95° C. for 10 hours. After cooling to room temperature, the DMF solution was poured into 1000 mL of stirred water to precipitate the poly-β-cyclodextrin (PCD) as a fine, white, free-flowing powder. The precipitate was collected by suction filtration, washed thoroughly with water, and subjected to the Standard Drying Protocol. A yield of 46 grams of PCD was obtained form the procedure. The PCD was used without further purification to determine the relative binding affinities of MPT and PNP as described below.

A 50 mL aliquot of Stock 100 μM MPT and a 50 mL aliquot of Stock 100 μM PNP were mixed in a flask containing a Teflon® stirbar. A 100 mg quantity of PCD was added and the flask was sealed and the contents stirred at room temperature (23±2° C.). Every 30 minutes, the stirring was stopped and the solid PCD was allowed to settle. A sample of the supernatant was obtained and its absorbance at 275 m was measured. The sample was then returned to the flask, which was again sealed and stirred until the time to take the next sample. The cycle was repeated until successive absorbance measurements differed by less than 0.005 units, signifying that equilibrium had been reached. At this point, a 600 μL sample of solution was removed and diluted with 900 μL of 1 M NaOH(aq) solution. The absorbance of this solution was read at 405 nm. From these absorbance readings, the concentrations of MPT and PNP remaining in the solution were calculated using the calibration cures prepared for the Standard Enzyme Activity Assay. Equilibrium concentrations of [MPT] ~16 μM and [PNP] ~46 μM were measured in the solution in this manner. Consequently, the PCD bound ~34 μM MPT and ~4 μM PNP.

The equilibria occurring in the solution in the presence of the solid PCD are defined in equations (3) and (4) below, where [MPT] and [PNP] are the equilibrium concentrations of MPT and PNP, respectively, in solution. $K_m$ and $K_p$ are the equilibrium binding constants of MPT and PNP, respectively, by the PCD.

$$MPT+PCD \leftrightarrow MPT-PCD \quad K_m=[MPT-PCD]/([MPT][PCD]) \qquad (3)$$

$$PNP+PCD \leftrightarrow PNP-PCD \quad K_p=[PNP-PCD]/([PNP][PCD]) \qquad (4)$$

Combining equations (3) and (4) gives Equation (5).

$$S=K_m/K_p=([MPT-PCD]/[MPT])\times([PNP]/[PNP-PCD]) \qquad (5)$$

The term S in equation (5) represents the preference of the PCD for binding MPT over PNP. The concentration of MPT bound in the PCD, [MPT–PCD], is simply the difference between the initial concentration of MPT in solution, [MPT]$_0$, and the concentration remaining at equilibrium, [MPT], as shown in equation (6).

$$[MPT-PCD]=[MPT]_0-[MPT]=50\ \mu M-16\ \mu M=34\ \mu M \qquad (6)$$

Likewise, the concentration of PNP bound in the PCD, [PNP–PCD], is simply the difference between the initial concentration of PCD in solution, [PCD]$_0$, and the concentration remaining at equilibrium, [PCD], as shown in equation 7.

$$[PNP-PCD]=[PNP]_0-[PNP]=50\ \mu M-46\ \mu M=4\ \mu M \qquad (7)$$

Substitution of equations (6) and (7) into equation (5) yields equation (8).

$$S=K_m/K_p=(([MPT]_0-[MPT])/[MPT])\times([PNP]/([PNP]_0-[PNP])) \qquad (8)$$

Using equation (8) and the measured concentrations of [PNP]$_0$=[MPT]$_0$=50 μM, [MPT] ~16 μM, and [PNP] ~46 μM, we calculate S ~24. Therefore, both MPT and PNP are bound by the PCD resin and binding of MPT is favored by a factor of ~24 over binding of PNP in the PCD resin.

Example 25

Fabrication of a Multilayercoated Cotton Cloth Functionalized with β-Cyclodextrin having a Single OPH Enzyme Layer This example describes the functionalization of a cotton cloth with β-cyclodextrin and the use of said functionalized cotton cloth as a platform for fabrication of a multilayer film bearing a single layer of OPH enzyme.

A square piece of cotton cloth (Hanes Inc.) of size ~8 inches×8 inches was placed in a 1000 mL Erlenmeyer flask equipped with Teflon® stirbar. A solution containing ~10 grams (~8.81 mmole) of β-cyclodextrin and ~13 grams (~77.3 mmole) of DICH in ~200 mL of N,N-dimethylformamide (DMF) was added to the flask. The contents were then heated at 90-95° C. for 4 hours. After the flask cooled to room temperature, the PCD-functionalized cotton cloth (CC-PCD) was removed and washed successively with methanol, dichloromethane, acetone, and then copiously with water. The treated cloth was then cured by baking in an oven at 120° C. for 2 hours and allowed to cool to room temperature. The experiment described in Example 1 was then repeated using the PCD-functionalized cotton cloth to fabricate the multilayer film by dip coating. The structure of the resulting multilayer film was CC-PCD/BPEI/OPH/BPEI. A Standard Enzyme Binding Assay indicated that ~1.41 μg OPH were deposited per mg of CC-PCD cloth.

Example 26

Fabrication of a Multilayercoated Cotton Cloth Functionalized with an Aminoalkylsiloxane Film having a Single OPH Enzyme Layer This example describes the functionalization of cotton cloth with amine functional groups and the use of said functionalized cotton cloth as a platform for fabrication of a multilayer film bearing a single layer of OPH enzyme without the need to use an initial BPEI polymer layer.

A 1 gram (~4.50 mmole) quantity of N-[3-(trimethoxysilyl)propyl]ethylenediamine (TMSED) was dissolved in 20 mL deionized water contained in a 50 mL plastic centrifuge tube. A piece of cotton cloth (~5 cm×5 cm) was placed in the solution and the tube was sealed and mounted on the wheel of a laboratory rotator. The sample was rotated for 20 min at a speed of ~60 rpm to thoroughly wet the cloth. At this point, 200 μL of concentrated ammonium hydroxide solution was added to the sample solution and agitation was continued using the rotator for 3 hours. The cotton cloth was then removed from the TMSED solution, washed 3 times with deionized water, and cured by baking in an oven at 125° C. for 2 hours. After the amine-functionalized cloth (CC-NH$_2$) had cooled to room temperature, a piece treated with ninhydrin solution produced a red color indicative of functionalization by amino groups. The experiment described in Example 1 was then repeated using the CC-NH$_2$ cloth with the omission of the first step involving deposition of the BPEI-w polyelectrolyte layer to fabricate the multilayer film by dip coating. The structure of the resulting multilayer film was CC-NH$_2$/OPH/BPEI. A Standard Enzyme Binding Assay indicated that ~1.53 µg OPH were deposited per mg of CC-NH$_2$ cloth.

Example 27

MPT Hydrolysis Activity of
β-Cyclodextrin-functionalized Cotton Cloth and
Unfunctionalized Cotton Cloth each Coated by a
Multilayer Film Containing a Single OPH Enzyme
Layer Prepared by Dip Coating This example demonstrates that a PCD-functionalized cotton cloth dip coated with a multilayer polyelectrolyte film encapsulating a single layer of OPH enzyme from Example 25 is capable of hydrolyzing MPT in solution to PNP at a faster rate than a standard CC/BPEI/OPH/BPEI film.

A CC/BPEI/OPH/BPEI cloth standard was prepared as described in Example 14. The Standard Enzyme Binding Assay indicated that ~1.77 µg OPH/mg cloth were bound. A piece of cotton cloth (CC) not treated by BPEI or OPH was also used. Pieces of CC, CC/BPEI/OPH/BPEI, and CC-PCD/BPEI/OPH/BPEI from Example 25, each of size ~5.0 cm×2.7 cm and weighing ~155 mg, ~158 mg, and ~191 mg, respectively, were prepared by cutting larger sized cloths. Each sample of cloth was placed in a separate 50 mL plastic centrifuge tube. A 20 mL aliquot of Stock 100 µM MPT solution was added to each centrifuge tube and the tubes were capped and agitated using the laboratory rotator. After 10, 30, 60, 120, 180, and 300 minutes, aliquots of solution were withdrawn from each tube and the [PNP] produced was measured using the Standard Enzyme Activity Assay. MPT hydrolysis activities for each sample were calculated using the initial slope (≡initial velocity) of plots of [PNP] versus time. For the CC, the activity was essentially zero (i.e., <0.01×10$^{-9}$ M·s$^{-1}$). For the CC/BPEI/OPH/BPEI sample, the initial velocity was ~1.0×10$^{-9}$ M·s$^{-1}$ (≡0.32 min$^{-1}$). For the CC-PCD/BPEI/OPH/BPEI sample, the initial velocity was ~1.8×10$^{-8}$ M·s$^{-1}$ (≡5.77 min$^{-1}$), a rate ~18 times faster than the CC/BPEI/OPH/BPEI sample.

Example 28

MPT Hydrolysis Activity of an
Amino-functionalized Cotton Cloth Coated by a
Multilayer Film Containing a Single OPH Enzyme
Layer Prepared by Dip Coating This example demonstrates that a amino-functionalized cotton cloth dip coated with a multilayer polyelectrolyte film encapsulating a single layer of OPH enzyme from Example 26 is capable of hydrolyzing MPT in solution to PNP at a comparable rate to the standard CC/BPEI/OPH/BPEI film.

The experiment of Example 27 was repeated using a sample of the CC-NH$_2$/OPH/BPEI (size ~5.0 cm×2.7 cm; weight ~168 mg) prepared according to Example 26. An initial velocity for the hydrolysis of MPT was ~1.3×10$^{-9}$ M·s$^{-1}$ (≡0.44 min$^{-1}$), comparable to that obtained for the CC/BPEI/OPH/BPEI sample in Example 27.

Example 29

PNP Binding Ability of
β-Cyclodextrin-functionalized Cotton Cloth

This example demonstrates that the CC-PCD sample prepared in Example 25 binds PNP.

Pieces of CC, CC-PCD prepared from Example 25, and CC-NH$_2$ prepared from Example 26, each of size ~5.5 cm×1.5 cm and weighing ~89 mg, ~107 mg, and ~104 mg, respectively, were prepared by cutting larger sized cloths. Note that these samples are not coated with the BPEI/OPH/BPEI multilayers. Each sample of cloth was placed in a separate 50 mL plastic centrifuge tube. A 5 mL aliquot of Stock 100 µM PNP solution was added to each centrifuge tube and the tubes were allowed to stand overnight for 16 hours. The cloth samples were removed from each PNP solution and the [PNP] remaining in solution was measured using the procedure described for the Standard Enzyme Activity Assay. A [PNP]>99 µM was measured for solutions containing the CC and CC-NH$_2$ samples, indicating that essentially no PNP was adsorbed to these materials. In contrast, [PNP] ~87 µM was measured for the solution containing the CC-PCD sample, indicating that PNP adsorption had occurred. The amount of PNP adsorbed by the CC-PCD sample was ~3.9×10$^{-9}$ moles PNP/cm$^2$ CC-PCD (≡6.1×10$^{-10}$ moles PNP/mg CC-PCD).

Example 30

Preparation of a β-Cyclodextrin-functionalized
Polyelectrolyte

This example describes the synthesis of a polyelectrolyte bearing covalently attached β-cyclodextrin group for use in fabrication of polyelectrolyte-enzyme multilayer films on substrates.

A BPEI polyelectrolyte bearing pendant β-cyclodextrin groups covalently attached to the polymer amine groups was prepared via slight modification of the literature methods (G. Crini, G. Torri, M. Guerrini, B. Martel, Y. Lekchiri, M. Morcellet, "Linear Cyclodextrin-poly(vinylamine): Synthesis and NMR Characterization," *Eur. Polym. J.*, 33 (7) 1143-1151 (1997); and A. Ruebner, G. L. Statton, M. R. James, "Synthesis of a linear polymer with pendent γ-cyclodextrins," *Macromol. Chem. Phys.*, 201, 1185-1188 (2000), the entire contents of both are incorporated herein by reference) as follows: Mono-6-Tolylsulfonyl-6-deoxy-β-cyclodextrin (TCD) was first prepared by dropwise addition of a solution of 0.151 g p-toluenesulfonyl chloride (0.792 mmol) in 5 ml pyridine to a stirred solution of 1.0 g β-cyclodextrin (0.88 mmol) in 5 ml pyridine at 5° C. under an atmosphere of dry N$_2$. Following the addition, the solution was stirred for a further 48 hours at 5° C. under an atmosphere of dry N$_2$. After evaporation of the solvent, the residue was washed repeatedly with water and acetone followed by drying under vacuum at 60° C. affording 0.388 g (38%) of product. The tosylated cyclodextrin was analyzed in a solvent system of butanol-ethanol-ammonium hydroxide-water 5:4:4:3. Spots were visualized by staining and heating with an anthrone solution (0.1 wt-% anthrone in H$_2$SO$_4$ diluted 1:50 with ethanol). A single spot on TLC gave a R$_f$=0.75. $^1$H NMR (400 MHz, DMSO-d$_6$): 7.7-7.4 (AA'BB' 4 H); 5.74 (m, 14 H); 4.78-4.79 (m, 7 H); 3.59-3.21, (m, CD protons), 2.52 (s, 3 H). $^{13}$C NMR (100 MHz CDCl$_3$) 145.1, 133.0, 130.2, 127.9, 102.3, 81.9, 73.3, 72.7, 72.3, 60.2, 21.5. TOFHRMS: calculated for C$_{49}$H$_{76}$O$_{37}$S, 1288; found, 1289.

Polyethylenimine with 1.2% pendent β-cyclodextrins (BPEI-CD) was then prepared by dropwise addition of a solution of 0.300 g TCD (0.232 mmol) in 3 mL DMSO to a stirred solution of 0.300 g polyethylenimine in 7 mL DMSO at 60° C. for 48 hours. The crude product was purified by membrane filtration. The residue was freeze-dried affording 0.355 g (59.0% yield based on addition of BPEI). The BPEI-CD polymeric system formed was analyzed in a solvent system of butanol-ethanol-ammonium hydroxide-water 5:4:4:3. Spots were visualized by staining and heating with an anthrone solution (0.1 wt-% anthrone in H$_2$SO$_4$ diluted 1:50 with ethanol). A single spot on TLC gave an R$_f$=0.0. $^1$H NMR (400 MHz, D$_2$O): 4.79 (bs, 7 H), 3.59-3.2 (m, CD protons), 2.92-2.57 (m, PEI). By adjusting the ratios of PEI and CD, polyethylenimine with 2.1% β-cyclodextrin loading (BPEI:CD=0.250 g: 0.500 g; $^1$H NMR (400 MHz, D$_2$O): 4.79 (bs, 7 H), 3.59-3.2 (m, CD protons), 2.92-2.57 (m, BPEI)) or 3.6% β-cyclode loading (BPEI:CD=0.250 g: 1.00 g; $^1$H NMR (400 MHz, D$_2$O): 4.79 (bs, 7 H), 3.59-3.2 (m, CD protons), 2.92-2.57 (m, BPEI)) were also obtained.

The CD loading on the BPEI-CD polymers was determined using the anthrone-CD sugar interaction. A calibration curve was measured with cyclodextrin in a concentration range of 0.01-4.1 mg CD/mL water. A solution of 0.1 g anthrone in 100 ml conc. H$_2$SO$_4$ was prepared. Sample solutions were prepared by dissolving 10-20 mg BPEI-CD sample in 100 mL water. 1 mL of the sample solution and 2.5 ml anthrone solution were transferred into a tube and heated in a water bath at 60° C. for 10 minutes. The solutions were cooled to room temperature with cold water and an UV-VIS spectrum was recorded immediately. The reference cuvette contained a blank sample (1 mL water+2.5 mL anthrone solution). The absorbance at a wavelength of 625 nm was measured. The cyclodextrin content of the sample was determined from the calibration curve.

Example 31

Fabrication and MPT Hydrolysis Activity of Cotton Cloth Coated with a β-Cyclodextrin-functionalized Polyelectrolyte-OPH Enzyme Multilayer Prepared by Dip Coating This example demonstrates the ability to coat cotton cloth with a β-cyclodextrin-functionalized polyelectrolyte-OPH enzyme multilayer and use said coated cloth for the hydrolysis of MPT in solution.

The experiment of Example 1 was repeated using a fresh piece of cotton cloth as the substrate with the following modification. The BPEI polyelectrolyte in the BPEI-w and BPEI-b solutions was replaced by the corresponding BPEI-CD polymer prepared in Example 30. The resulting film had the structure CC/BPEI-CD/OPH/BPEI-CD. Separate cloth samples were prepared using β-cyclodextrin-functionalized BPEI having 2.1% and 3.6% β-cyclodextrin loadings. In each case, the concentration of the BPEI-CD solution used to treat the cloth was 1.2 mg BPEI-CD/mL aqueous or BTP buffer solution. For each cloth, MPT hydrolysis activity was tested by placing a cloth sample (Weight ~159 mg; Size ~5.0 cm×2.5 cm) in a 20 mL volume of Stock 100 μM MPT solution in a centrifuge tube and agitating using the laboratory rotor. The Standard Enzyme Activity Assay was performed to determine the extent of MPT hydrolysis as a function of time. For the CC/BPEI-CD/OPH/BPEI-CD sample loaded at the 2.1% level with β-cyclodextrin, an initial velocity of 2.6×10$^{-9}$ M·s$^{-1}$ was observed at 23±2° C. After ~22 hours, the amount of PNP produced was ~76 μM, indicating substantial hydrolysis of the MPT. For the CC/BPEI-CD/OPH/BPEI-CD sample loaded at the 3.6% level with β-cyclodextrin, an initial velocity of 2.8×10$^{-9}$ M·s$^{-1}$ was observed at 23±2° C. After ~22 hours, the amount of PNP produced was ~82 μM. A control CC/BPEI/OPH/BPEI cloth, prepared using the same OPH solution and at the same time as the CC/BPEI-CD/OPH/BPEI-CD samples, gave an initial velocity of ~1.4× 10$^{-9}$ M·s$^{-1}$ and produced ~59 μM PNP after 22 hours.

Example 32

Vapor Phase MPT Hydrolysis Activity of Multilayercoated Cotton Cloth Containing a Single OPH Enzyme Layer Prepared by Dip Coating This example demonstrates that cotton cloth coated with a multilayer polyelectrolyte film encapsulating a single layer of OPH enzyme is capable of hydrolyzing MPT vapors to PNP at 40° C.

A piece of cotton cloth coated with a multilayer film (weight ~152 mg; size ~5.2 cm×2.5 cm) as described in Example 14 of structure CC/BPEI/OPH/BPEI was attached by a piece of string to the underside of a lid for a jar of volume ~1330 cm$^3$. A Petri dish containing 5.2 mg solid MPT was placed in the jar and a 500 μL drop of water was placed inside the jar on the floor. The jar was sealed with the lid such that the CC/BPEI/OPH/BPEI sample was suspended ~2 cm above the MPT in the Petri dish inside the jar. The entire assembly was placed in a water bath held at 40±1° C. and observed. After 6 days, the cloth exhibited a noticeable, but pale, yellow tint. By the seventh day, the cloth was clearly yellow in color, suggesting that hydrolysis of MPT vapor had occurred on or in the multilayer film coating the cloth. Hydrolysis was confirmed by removing the cloth from the jar and extracting it twice with 2 mL portions of methanol. The yellow methanol extracts were combined and allowed to evaporate to dryness, yielding a yellow residue. The residue was taken up in 3 mL CHES-m buffer solution and analyzed according to the procedure of the Standard Enzyme Activity Assay. From the solution absorbances measured at 275 nm and 405 nm, it was shown that ~102 μg MPT and ~10 μg PNP were present, consistent with adsorption of MPT vapor and its hydrolysis to PNP by the CC/BPEI/OPH/BPEI sample.

The above description is that of a preferred embodiment of the invention. Various modifications and variations are possible in light of the above teachings. It is therefore to be understood that, within the scope of the appended claims, the invention may be practiced otherwise than as specifically described. Any reference to claim elements in the singular, e.g. using the articles "a," "an," "the," or "said" is not construed as limiting the element to the singular.

The invention claimed is:

1. A catalytic enzyme-modified substrate for providing protection against chemical agents, comprising:
   (a) a substrate which absorbs charged polymer components;
   (b) a polyelectrolyte layer deposited onto the substrate;
   (c) an enzyme layer deposited onto the polyelectrolyte layer to degrade a chemical agent;
   (d) a capping layer deposited onto the enzyme layer; and
   (e) optionally a base layer deposited onto the capping layer, a second polyelectrolyte layer deposited onto the base layer, a second enzyme layer deposited onto the second polyelectrolyte layer, and a second capping layer;

wherein the optional layers in (e) may be repeated any number of times.

2. The catalytic enzyme-modified substrate of claim 1, wherein said substrate comprises fiberglass, cotton, rayon, nylon, or any combination thereof.

3. The catalytic enzyme-modified substrate of claim 1, wherein said substrate comprises unmodified cotton, cotton modified with cyclodextrin, cotton modified with an amine, or any combination thereof.

4. The catalytic enzyme-modified substrate of claim 1, wherein said substrate comprises a material whose surface has been chemically modified to generate functional groups that can support adsorption of charged polymer components.

5. The catalytic enzyme-modified substrate of claim 3, wherein said substrate comprises polytetrafluoroethylene (PTFE) that has been oxidized.

6. The catalytic enzyme-modified substrate of claim 1, wherein said substrate is a thread that is woven into a fabric after deposition of the final capping layer.

7. The catalytic enzyme-modified substrate of claim 1, wherein said polyelectrolyte layer comprises a β-cyclodextrin-functionalized polyelectrolyte.

8. The catalytic enzyme-modified substrate of claim 1, wherein said enzyme layer comprises organophosphorous hydrolase (OPH), organophosphorous acid anhydrolase (OPAA), DFPase, phosphotriesterases (PTE), or any combination thereof.

9. The catalytic enzyme-modified substrate of claim 1, wherein said polyelectrolyte layer comprises branched or linear polyethyleneimine (PEI), polyacrylic acid (PAA), polymethacrylic acid (PMA), polystyrene sulfonate (PSS), polydiallyl dimethyl ammonium chloride (PDDA), polyvinylpyridine (PVP), polyvinyl sulfate (PVS), polyallylamine hydrochloride (PAH), their chemically altered derivatives, or any combination thereof.

10. The catalytic enzyme-modified substrate of claim 1, wherein said capping layer comprises a readily polymerizable monomer.

11. The catalytic enzyme-modified substrate of claim 1, wherein said capping layer comprises polystyrene sulfonate (PSS), branched polyethylenimine (BPEI), 1,2-dihydroxypropyl methacrylate (DHPM), 1,2-dihydroxypropyl 4-vinylbenzyl ether (DHPVB), N-[3-trimethoxysilyl)propyl] ethylenediamine (TMSED), or any combination thereof.

12. The catalytic enzyme-modified substrate of claim 1, wherein said layers are deposited using dip coating, spin coating, spray coating, or any combination thereof.

13. The catalytic enzyme-modified substrate of claim 1, wherein the outermost capping layer is a bactericidal layer.

14. The catalytic enzyme-modified substrate of claim 13, wherein said outmost capping layer comprises branched polyethylenimine (BPEI) modified with a hexyl group and quaternized with methyl bromide.

15. A catalytic enzyme-modified substrate for providing protection against chemical agents, comprising:
(a) a substrate comprising cotton modified with an amine;
(b) an enzyme layer deposited onto the substrate to degrade a chemical agent;
(c) a capping layer deposited onto the enzyme layer; and
(d) optionally a base layer deposited onto the capping layer, a second enzyme layer deposited onto the base layer, and a second capping layer;

wherein the optional layers in (d) may be repeated any number of times.

* * * * *